US006285452B1

(12) United States Patent
Baker

(10) Patent No.: US 6,285,452 B1
(45) Date of Patent: Sep. 4, 2001

(54) PORTABLE SCANNING SPECTROPHOTOMETER

(75) Inventor: Douglas V. Baker, Middleville, MI (US)

(73) Assignee: X-Rite Incorporated, Grandville, MI (US)

( * ) Notice: Subject to any disclaimer, the term of this patent is extended or adjusted under 35 U.S.C. 154(b) by 0 days.

(21) Appl. No.: 09/704,005

(22) Filed: Nov. 1, 2000

Related U.S. Application Data

(63) Continuation of application No. 09/341,156, filed as application No. PCT/US98/18108 on Sep. 1, 1998, now Pat. No. 6,198,536.

(51) Int. Cl.[7] ....................................................... G01J 3/51
(52) U.S. Cl. .......................................... 356/402; 250/226
(58) Field of Search ..................................... 356/319, 326, 356/328, 402, 405, 406, 416, 418, 419, 429, 430, 431; 250/226

(56) References Cited

U.S. PATENT DOCUMENTS

| | | |
|---|---|---|
| 4,243,319 | 1/1981 | Lodzinski . |
| 4,944,594 | 7/1990 | Burk . |
| 5,062,714 | 11/1991 | Peterson et al. . |
| 5,118,183 | 6/1992 | Cargill et al. . |
| 5,307,155 | * 4/1994 | Ando et al. ........................... 356/430 |
| 5,369,494 | 11/1994 | Bowden et al. . |
| 5,373,364 | 12/1994 | Krzyminski . |
| 5,646,735 | 7/1997 | Krzyminski . |
| 6,157,730 | * 12/2000 | Roever et al. ........................ 382/110 |

FOREIGN PATENT DOCUMENTS

| | | |
|---|---|---|
| 19633557A1 | 3/1998 | (DE) . |
| 19716066C1 | 9/1998 | (DE) . |

OTHER PUBLICATIONS

"All–In–One Desktop Spectrophotometer", (X–Rite, Incorporated—Copyright 1999—Acknowledged as prior art).
"Spectrolino Spectrophotometer", (Gretag Macbeth—Mar. 1998—Acknowledged as prior art).
"Gretag Spectrolino SpectroScan Operating Manual", (Gretag—Undated—Acknowledged as prior art).

* cited by examiner

Primary Examiner—F. L. Evans
(74) Attorney, Agent, or Firm—Warner Norcross & Judd

(57) ABSTRACT

The specification discloses a portable spectrophotometer (10) providing improved movement and control of the sample (S) during analysis. The unit (10) includes a base (12) and an upper assembly (14) supported on the base (12) for floating movement. Both a spectral measurement engine (20) and drive rollers (104) are contained within the upper assembly. The base (12) includes independently suspended idler rollers (16), and the drive rollers (104) engage the idler wheels (16), so that at least a portion of the weight of the upper assembly (14) is borne by the engaging drive rollers (104) and idler rollers (16). The upper assembly (14) therefore floats up and down with samples (S) of varying thickness moving between the rollers (104 and 16). Additional upstream idler rollers (18 and 24) on the base and the upper assembly engage one another and bear a portion of the weight of the upper assembly (14) to create tension in opposition to the drive rollers (104) to hold the sample (S) taut. A planar media guide (130) is located on the underside of the upper assembly (14) and surrounds the spectral engine (20) to engage the sample (S) and reduce flexing and bowing of the sample (S). A manually actuated backer (30) is supported by the base (12) to selectively present to the spectral engine (20) one of two areas (52a and 52b) with different reflective properties. The unit (10) may include a first light source (21) in the spectral engine and a second light source (60) in the backer (30) so that the spectrophotometer (10) is capable of both reflective and transmissive analysis.

4 Claims, 7 Drawing Sheets

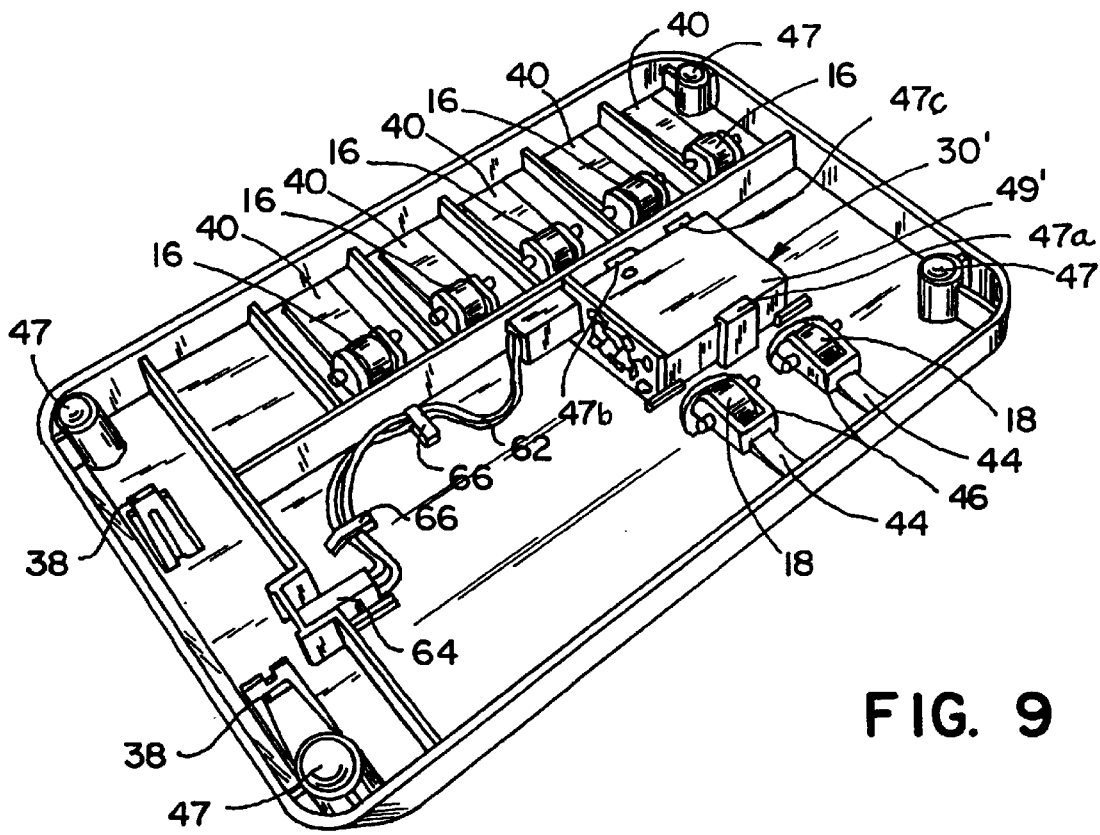
FIG. 9
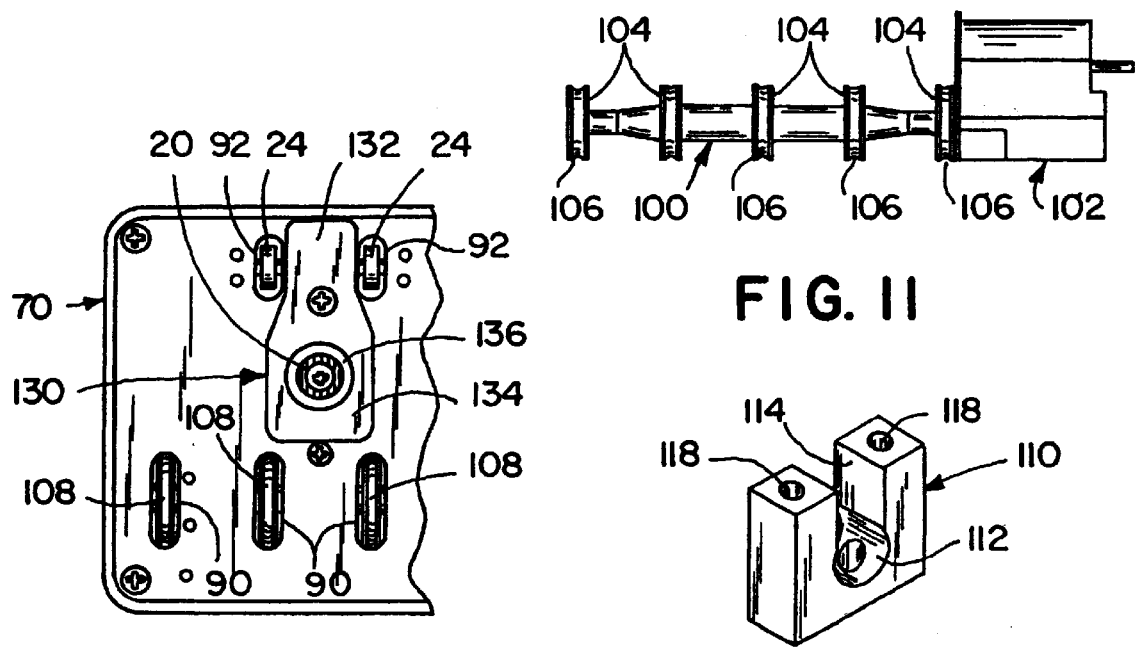
FIG. 11
FIG. 13
FIG. 12

PORTABLE SCANNING SPECTROPHOTOMETER

This is a continuation of application Ser. No. 09/341,156, filed Jul. 2, 1999 (now U.S. Pat. No. 6,198,536 which is 371 of PCT/US98/18108 filed on Sep. 1, 1998.

TECHNICAL FIELD

The present invention relates to color measurement instruments, and more particularly, to spectrophotometers.

BACKGROUND ART

Color measurement instruments for many and varied applications are well known. These instruments are used, for example, to determine color consistency in printed material, photographic material, textiles, and plastics. The most comprehensive color measurements are obtained by instruments known as spectrophotometers, which measure the spectral distribution of light and give a percentage reflection or transmission at many segments in the visible color spectrum.

The field of desk top publishing has expanded greatly in recent years, and color output devices such as color printers, plotters, proofers have become widely used. The color output devices are often controlled by computer software, which transmits control signals to the printer defining color to be produced. To assure color quality, it is desirable to be able to calibrate color printers to produce a selected quality of color for printed material produced by a number of different printers. Additionally, data defining a color product may be transmitted to remote locations to be printed by a variety of printers. In order to be able to provide a product of consistent color characteristics, a comparison to a color standard is required. All of these functions require the accurate measurement of many samples of different colors produced on the device. These colors are produced using only a few colorants—usually cyan (C), magenta (M), yellow (Y), and black (K).

A color measurement instrument, such as a spectrophotometer, includes a color measurement engine having an optical pick-up. Additionally, many instruments include a drive mechanism for moving either the sample or the engine to effect relative movement between the two. The registration of the sample with respect to the engine and the controlled movement of the sample or the engine are critical components in obtaining consistent and accurate measurements. Only small changes in the distance between the sample and the measurement engine can create significant errors and inconsistencies in the color measurement.

Prior color measurement instruments are illustrated in U.S. Pat. No. 5,369,494 issued Nov. 29, 1994 and entitled "Portable Scanning Colorimeter"; U.S. Pat. No. 5,118,183 issued Jun. 2, 1992 and entitled "Automated Strip Reader Densitometer"; and U.S. Pat. No. 5,062,714 issued Nov. 5, 1991 and entitled "Apparatus and Method for Pattern Recognition." In these units, the sample drive mechanism is located in the base, while the color measurement engine is located in an assembly above the base. Because these two primary components are located in different housings, there is the possibility that sample registration and movement is not as precisely controlled as required for present day measurement. Accordingly, artisans continue to seek improved structures for maintaining improved consistency and accuracy in sample registration and movement.

DISCLOSURE OF INVENTION

The aforementioned issues are addressed in the present invention providing improved sample registration and movement within a portable spectrophotometer. The instrument contains a mechanical drive system that transports the sample past the measurement engine in a precise fashion.

First, the spectrophotometer includes a base and an upper assembly supported for floating movement on the base. Both the color measurement engine and the sample drive mechanism are located within the upper assembly. As the sample is drawn between the base and the upper assembly, the upper assembly can float with samples of various and varying thickness. This approach reduces or even eliminates the need for separate tensioning devices within the drive system, such as springs and/or close tolerances.

Second, the drive mechanism includes a plurality of drive wheels, and the base includes a plurality of independently suspended idler rollers, each of which engages and supports one of the drive wheels. The independently suspended rollers flex to accommodate samples of varying and various thicknesses.

In a third embodiment of the invention, the drive rollers are located "downstream" (in the direction of sample travel) from the color measurement engine. Tension rollers are provided upstream of the color measurement engine to at least partially resist movement of the sample in response to the drive rollers. The tension created within the sample improves its consistent maintenance in a uniform plane and therefore its consistent registration with the color measurement engine.

In a fourth embodiment of the invention, a planar, low-friction media guide is located on the underside of the upper assembly to engage the top surface of the sample. The thickness of the media is approximately the same as the distance that the drive wheels extend from the upper assembly, so that the media guide consistently engages the top surface of the sample. Therefore, the media guide improves the registration of the sample with respect to the color measurement engine; and the media guide assists the upper assembly in riding the top surface of the sample.

In a fifth embodiment, a two-position backer is provided in the base. The backer includes two separate areas with different reflective properties. The backer is readily manually movable so that either of the two areas can be aligned with the optical pickup of the color measurement engine. For example, the two areas may be white light diffusing opal and stable uniform black. In an alternative embodiment, the light diffusing opal may be illuminated for transmissive analysis.

In a sixth aspect of the invention, the spectropliotometer is capable of both reflective and transmissive analysis. A first light source is included within the color measurement engine and is activated only when reflective analysis is desired. A second light source is included within the base, is aligned with the color measurement engine, and is activated only when transmissive analysis is desired.

These and other objects, advantages, and features of the invention will be more readily understood and appreciated by reference to the description and the drawings.

BRIEF DESCRIPTION OF DRAWINGS

FIG. 9 is a perspective view of the underside of the base with an alternative backer capable of illuination;

FIG. 11 is a front elevation view of the drive shaft and motor;

FIG. 12 is an enlarged perspective view of the drive shaft bearing;

FIG. 13 is a fragmentary bottom plan view of the upper assembly showing the media guide.

MODE FOR CARRYING OUT THE INVENTION

Figure 10:
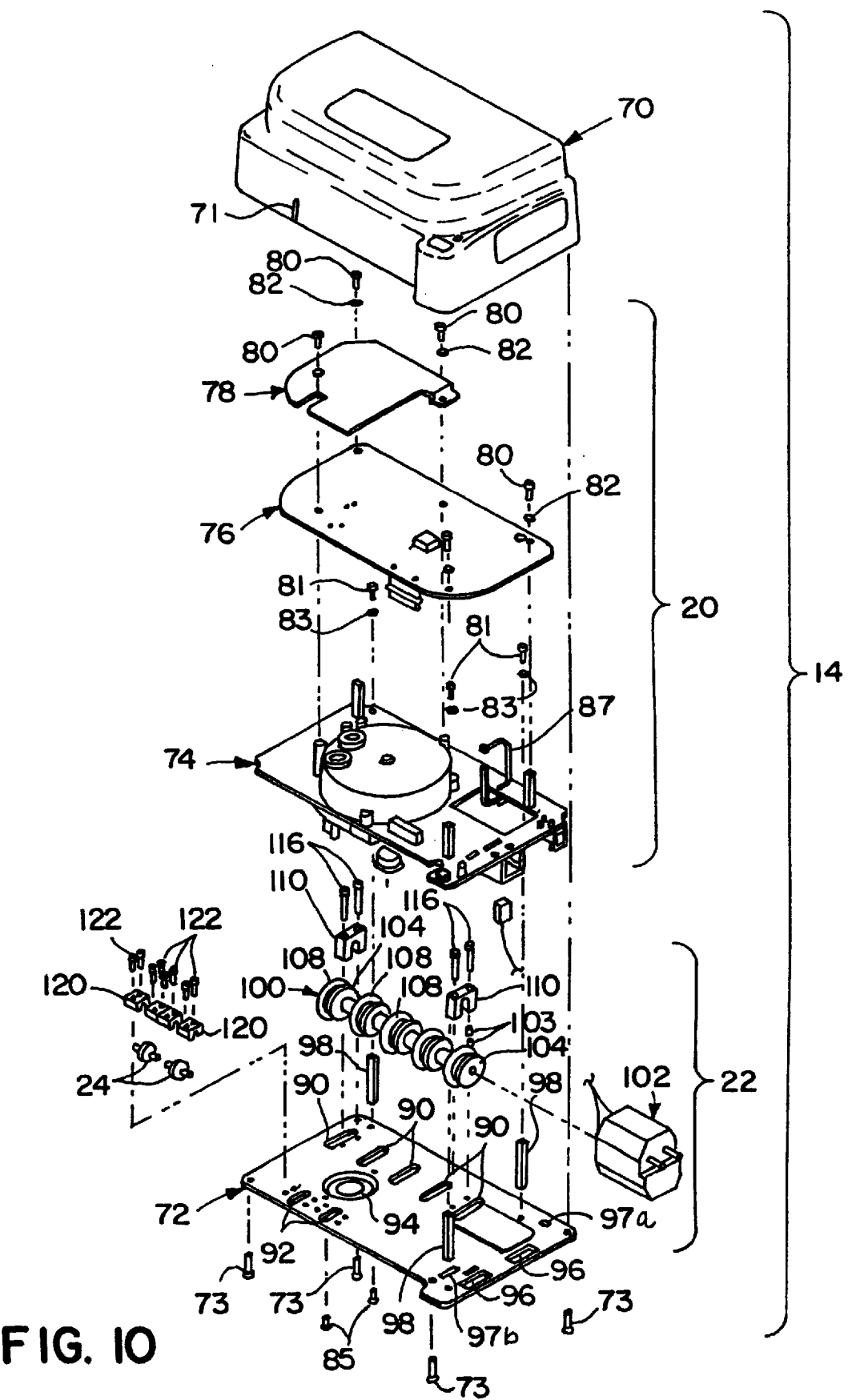
FIG. 10 is a perspective exploded view of the upper assembly.

A spectrophotometer constructed in accordance with a preferred embodiment of the present invention is illustrated in the drawings and generally designated 10. As perhaps best illustrated in FIGS. 3 and 10, the spectrophotometer includes a base 12 and an upper assembly 14 supported on the base. The base includes two sets 16 and 18 of idler rollers. The upper assembly 14 includes a spectral analysis engine 20, a drive assembly 22, and tension rollers 24. The engine 20 includes an optical pick-up 75. The drive rollers 22 of the upper assembly engage the idler rollers 16 of the base, and the tension rollers 24 of the upper assembly engage the idler rollers 18 of the base all to partially support the upper assembly 14 on the base 12. The drive rollers 22 pull or draw the sample S (see FIG. 1) through the spactrophotometer 10 and past the optical pick-up 75. The tension rollers 24 create a tension on the sample S to maintain the sample in a consistent plane.

I. Base

The base is perhaps best illustrated in FIGS. 3–8. Generally, the base 12 includes a body 26, idler rollers 16 and 18, and a backer 30.

The body 26 is plastic and includes a connector portion 32 and a sample portion 34. The connector portion 32 includes a platform 36, a pair of alignment pins 35a and 35b, and a pair of integrally molded spring clips 38. The platform 36 provides an engagement surface for the upper assembly 14. The pins 35a and 35b interfit. with apertures 97a and 97b (see FIG. 10) respectively to prevent relative rotation of the upper assembly 14 on the base 12 in a horizontal plane. The spring clips 38 include catches 39 (see FIG. 4) above the platform 36 and actuating portions 40 (see FIGS. 7 and 9) that extend through and below the platform. The actuating portions may be manually actuated from the underside of the base 12 to release the upper assembly 14 from the base 12.

The sample portion 34 of the base 12 is generally planar and supports the idler rollers 16 and 18 and the backer assembly 30. The forward edge 41 of the platform is rounded to facilitate insertion of the sample S between the base 12 and the upper assembly 14. A 35 mm groove or guide 43 in the forward edge 41 facilitates insertion and alignment of a strip of 35 mm film (not shown). A race-track shaped window 39 is defined in a central portion of the sample portion 34.

The body base includes integral fingers 47a, 47b, and 47c on its underside. The finger 47a is opposed to the fingers 47b and 47c, and the fingers slidingly receive the backer assembly 30 as will be described. A foot 45 is mounted at each of the four corners of the base body. Preferably, the feet are fabricated of a relatively high-friction material to assist in securely support the unit 10 on a smooth surface.

Figure 3:
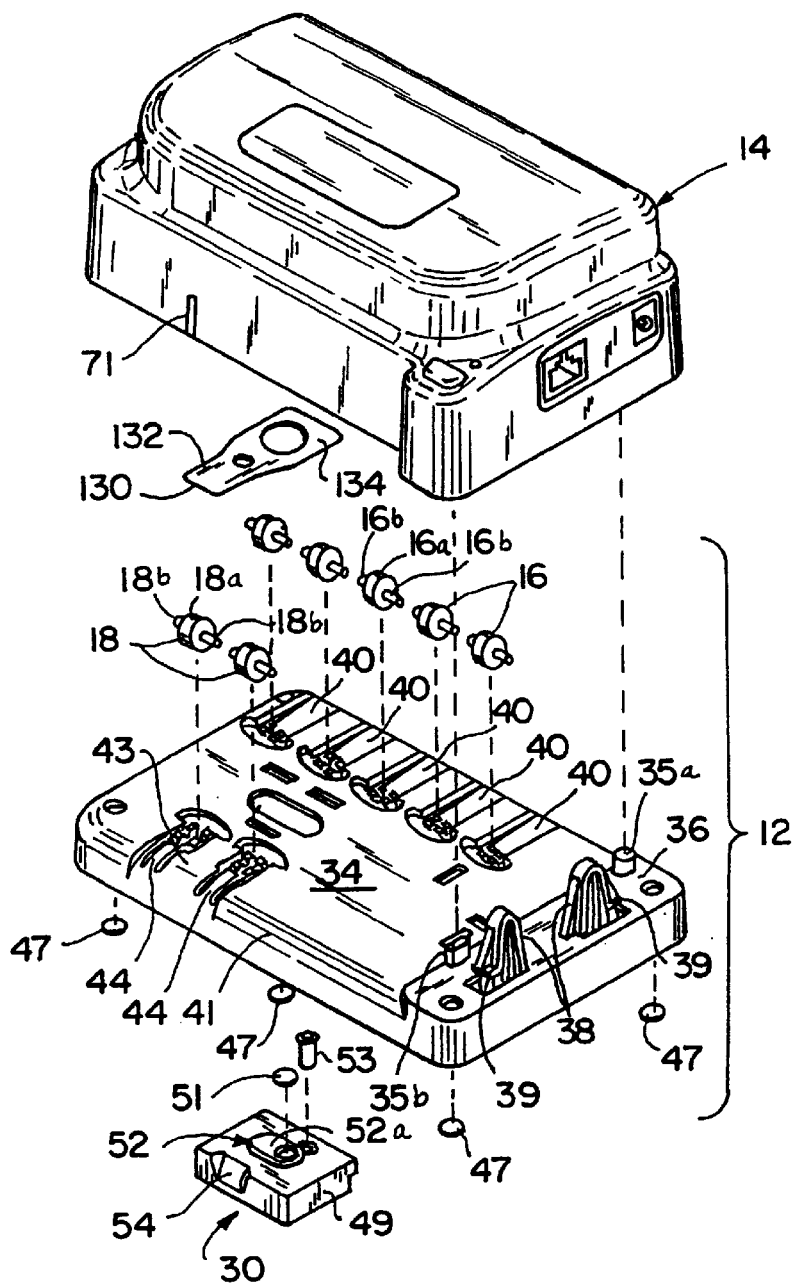
FIG. 3 is a a perspective view of the spectrophotometer with the base components exploded.

All of the idler rollers 16 and 18 are generally identical to one another. In the preferred embodiment, each is fabricated on plastic. As seen in FIG. 3, each includes a roller body 16a or 18a and a pair of stub shafts 16b or 18b extending therefrom.

Each of the rollers 16 is supported by a suspension arm 40. Each of the suspension arms 40 terminates in a bearing portion 42 which receives the stub shafts 16b and rotatably supports the associated roller 16. Each of the suspension arms 40 is integral with the remainder of the base body 26. The base 26 is fabricated of a resiliently flexible plastic, and therefore each of the arms 40 is resiliently deflectable downwardly under the weight of the upper assembly 14.

Similarly, each of the idler rollers 18 is supported for independent suspension on a suspension arm 44. Each of the suspension arms terminates in a bearing portion 46 for which receives the stub shafts 18b and rotatably supports the associated roller 18. As with arms 40, suspension arms 44 are resiliently deflectable in the downward direction under the weight of the upper assembly 14. When not deflected, the rollers 16 and 18 lie within and define a plane. The rollers 16 and 17 are retained in the bearing portions 42 and 46 because the stub shafts 16b and 18b extend under the sample portion 34. Any of the rollers 16 and 17 can be removed by pressing the supporting arm downwardly and lifting the roller from the bearing portion.

Figure 8:
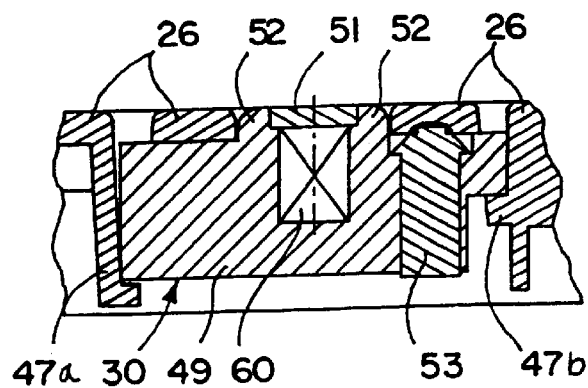
FIG. 8 is a sectional view taken along line VIII—VIII in FIG. 5.
Figure 4:
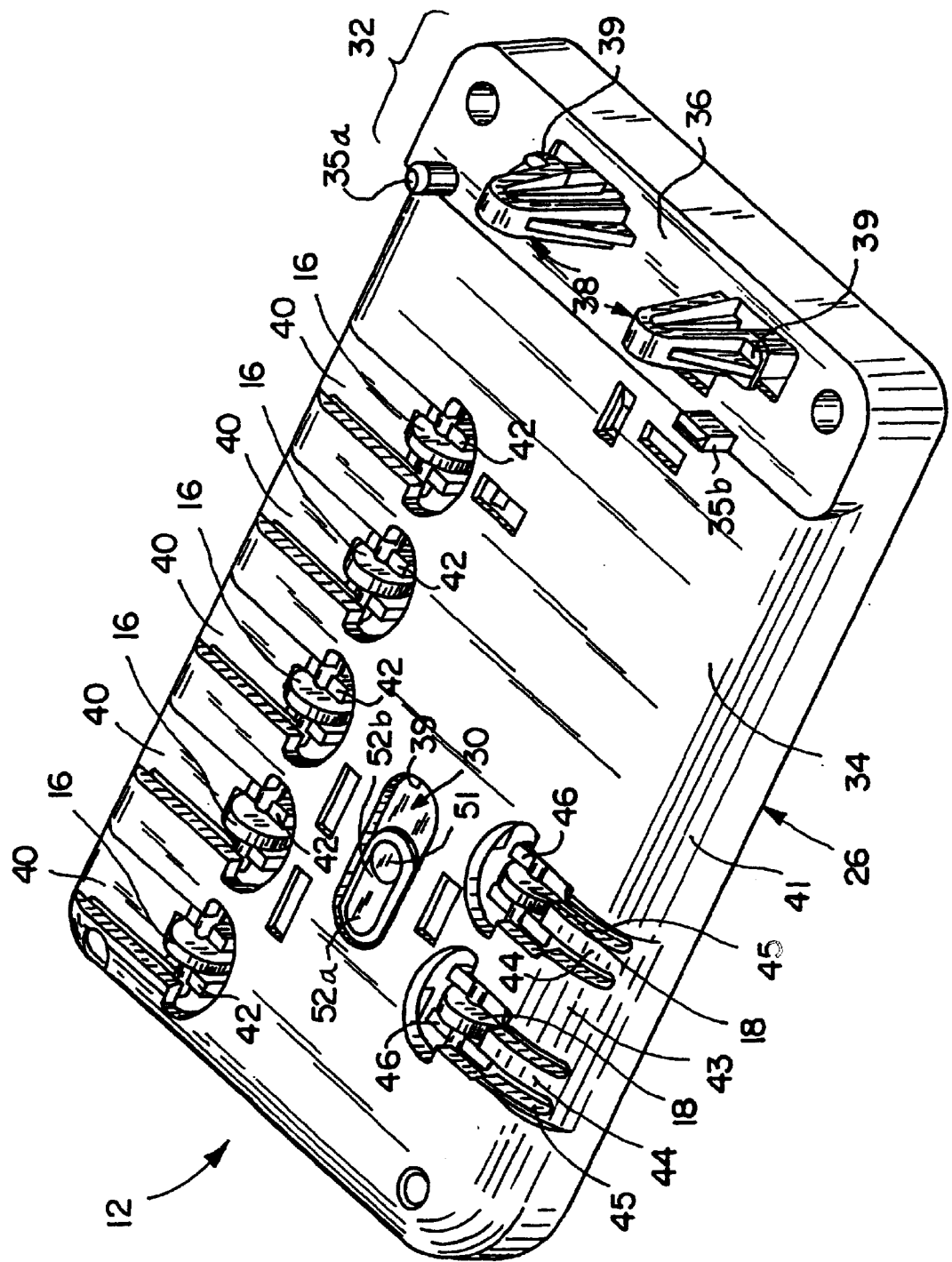
FIG. 4 is a perspective view of the base.
Figure 5:
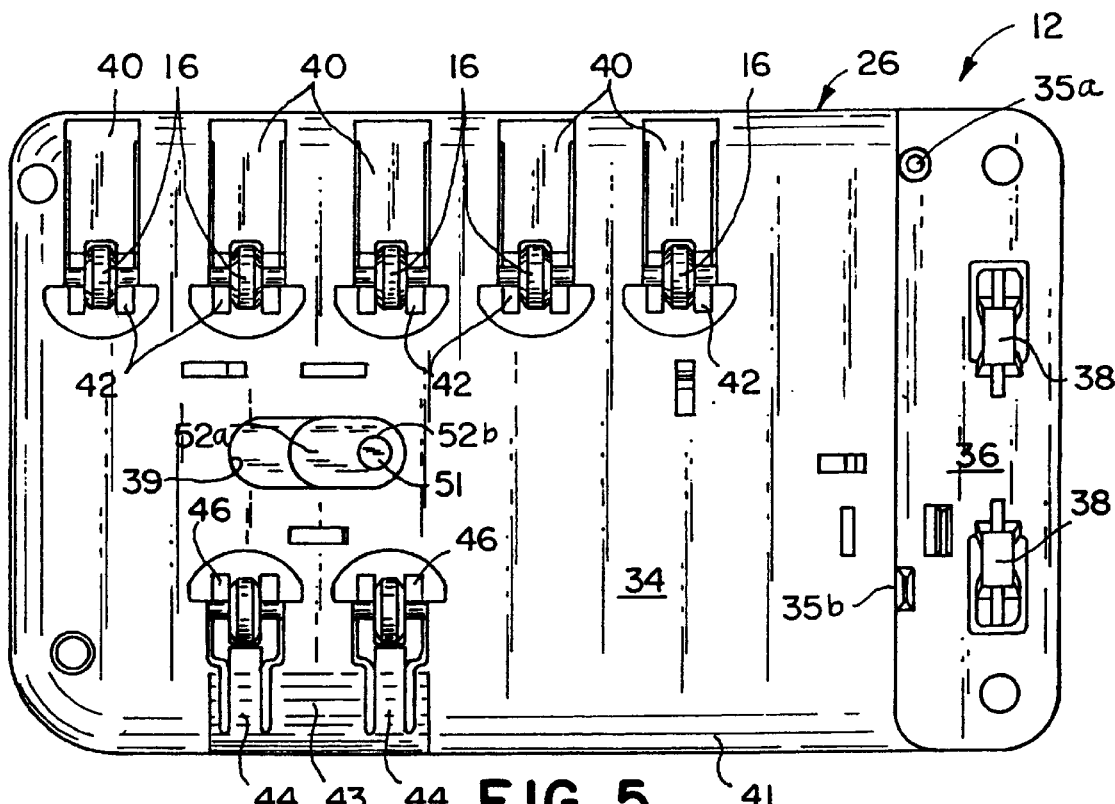
FIG. 5 is a top plan view of the base showing the backer in a first position.
Figure 6:
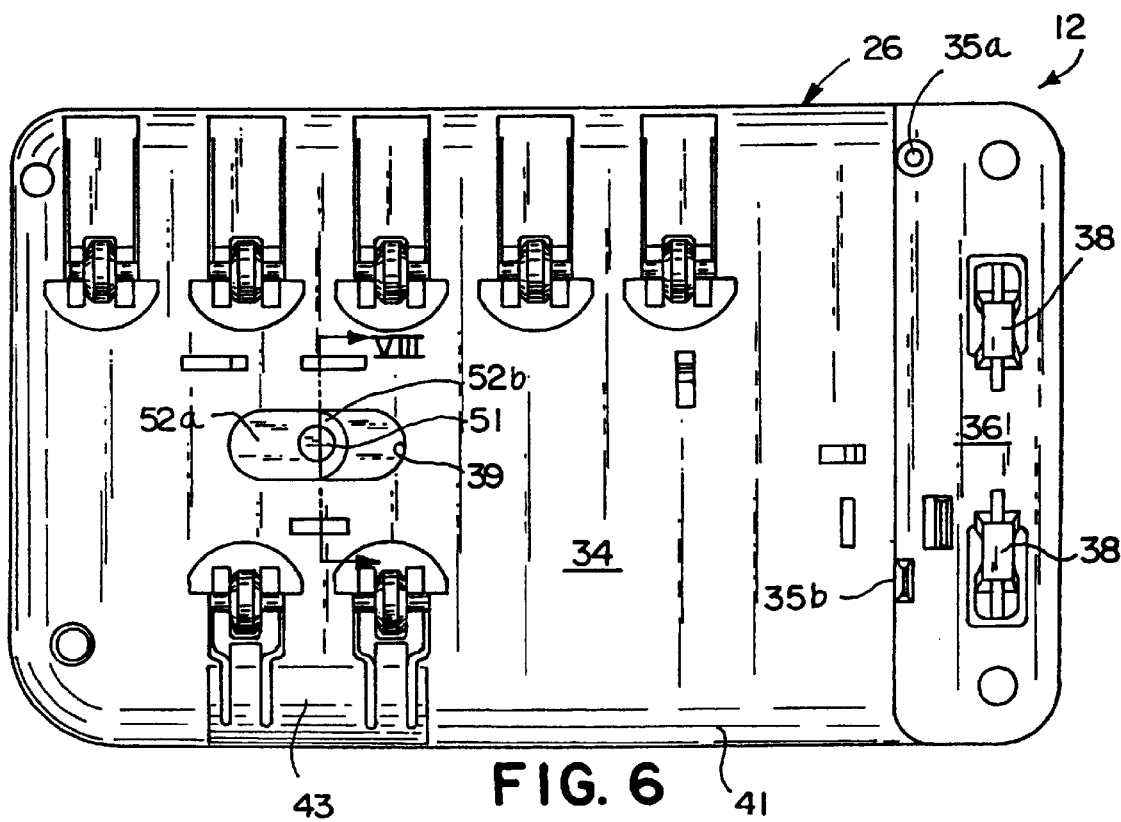
FIG. 6 is a top plan view of the base showing the backer in its second position.
Figure 7:
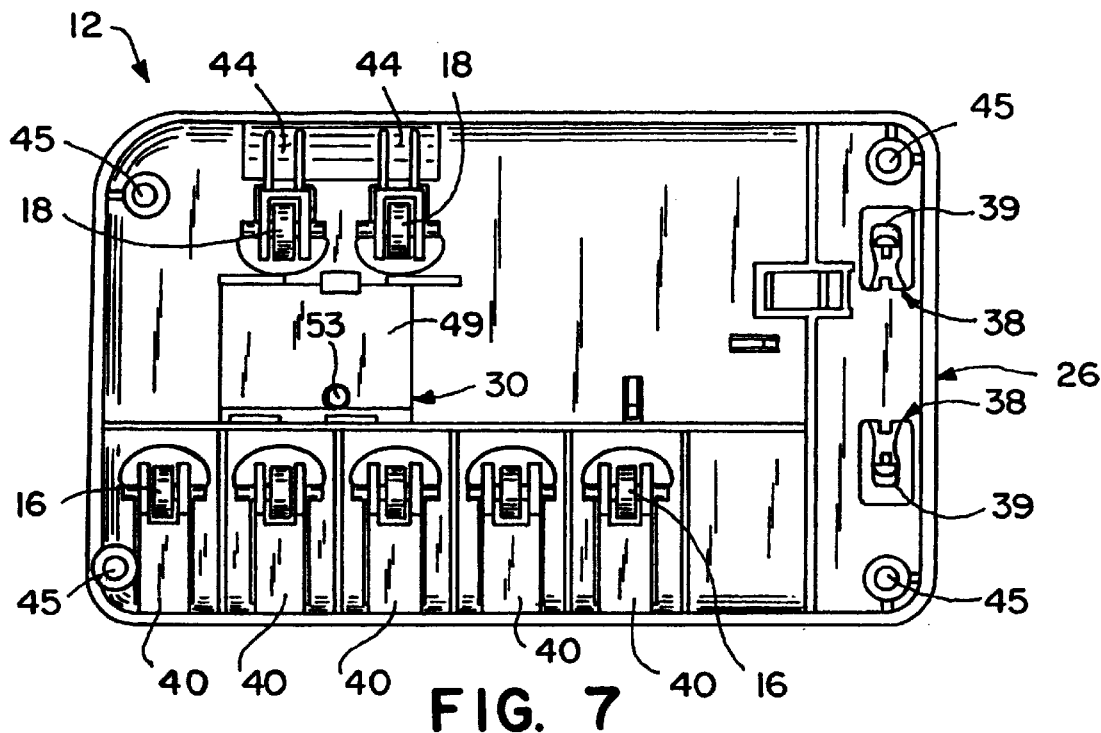
FIG. 7 is a-bottom plan view of the base showing the backer in the second position.

The backer assembly 30 is illustrated in FIGS. 3 and 7–8 and includes a body 49, a spring plunger 50, and an opal glass 51. The body 49 is held between fingers 47a on one side and 47b and 47c on the other side for sliding movement. The spring plunger 50 cooperates with detents (not visible) in the underside of the base body 26 to releasably catch the assembly in either of two opposite positions. The backer body 49 includes a recessed area 54 that facilitates removal of the backer assembly 30 from the base body 26 when the recessed area 54 is aligned with the finger 47a.

The body 49 includes a platform portion 52 extending upwardly from the remainder of the body 49 and into the window 39 of the base body 26. The platform provides two separate areas with different reflective properties. The first area 52a is stable uniform black. The second area 52b supports the white light diffusing opal glass 51. The white opal glass 51 is secured in position on the platform 52 using a solvent adhesive or other suitable interconnection means.

An alternative backer assembly 30' is illustrated in FIG. 9. The alternative backer assembly 30' is capable of providing illumination for operation of the spectrophotometer 10 in a transmissive mode of analysis. In the alternative backer 30', an illumination source 60 is positioned within the cavity 37 directly below the opal glass 51 (see FIG. 8). A power cord 62 extends from the backer assembly 30' and terminates in a plug 64 mounted within the backer base 26. The cord 62 is secured under wire management fingers 66, which are integral with the base body 26. The plug or connector 64 is held in position by the base body 26 for automatic connection with the upper assembly 14 when the upper assembly 14 is installed on the base 12.

II. Upper Assembly

The upper assembly 14 is illustrated in FIGS. 10–14. The upper assembly 10 includes a housing 70, a spectral measurement engine 20, a drive assembly 22, and a lower plate 72.

The housing 70 is injection molded of plastic to house the remaining upper assembly components. The housing includes an integral alignment mark 71 centered above the film strip guide 43 and linearly aligned with the spectral engine 20 to assist a user with properly aligning the sample S for scanning by the engine.

The spectral measurement engine 20 of the preferred embodiment is generally well known to those skilled in the art. For example, one suitable spectral engine is illustrated co-pending application Ser. No. 08/714,969 filed Sep. 17, 1996 by Berg et al and entitled "Compact Spectrophotometer," the disclosure of which is incorporated by reference. Other measurement engines, such as those for calorimeters and densitometers, can be used depending on the application. Generally speaking, the engine 20 includes an optics assembly 74, a printed circuit board (PCB) assembly 76, and a control board shield 78. The optics assembly 74 includes an optical pick-up 75 (see FIG. 14). The PCB assembly 76 and the shield 78 are secured to the optics assembly 74 using screws 80 and star lock washers 82. The optics assembly 74 is secured to the aluminum stand-offs on the bottom plate 72 using screws 81 and star lock washers 83. Additionally, the bottom plate 72 is secured to the optics assembly 74 using screws 85. The aluminum bottom plate 72 and the aluminum stand-offs 98 dissipate heat generated by the optics assembly and most notably by the illuminators 77. A wire tie 87 is included for wire management.

A plurality of illuminators 77 (see FIG. 14) are included within the spectral engine 20 to illuminate the sample S when the unit 10 is operated in the reflective analysis mode. The illuminators 77 are actuated only in the reflective mode (i.e. not in the transmissive mode).

The bottom plate 72 is generally planar, is fabricated of aluminum and provides an underside to the upper assembly 14. The perimeter of the bottom plate 72 is dimensioned to closely fit within the bottom of the housing 70. The plate 72 is secured to the housing 70 using screws 73.

The plate define two rectangular apertures 96 that receive the locking arms 38 of the base 12. When the upper assembly 14 is attached to the base 12, the catches 39 of the locking arms 38 engage the upper surface of the bottom plate to lock the upper assembly on the base; and the bottom plate 72 rests upon the platform 36 of the base 12 to at least partially support the weight of the upper assembly. The plate further defines two alignment apertures 97a and 97b that receive the alignment pins 35a and 35b respectively of the base 12. The interfit of the locking arms 38 within the apertures 96 and the interfit of the alignment pins 35 within the apertures 97 prevents the upper assembly from rotating in a generally horizontal plane, but permits the upper assembly to float or pivot in a generally vertical plane.

Figure 14:
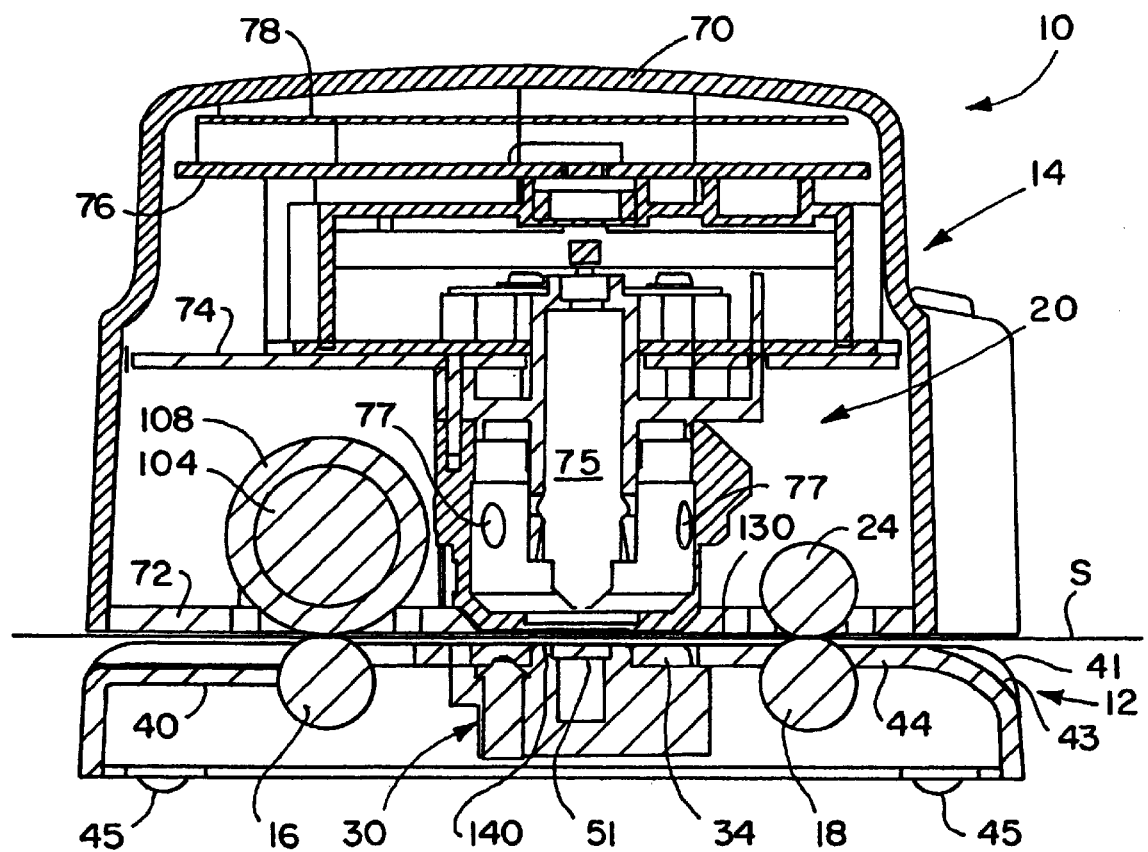
FIG. 14 is a sectional view of the spectrophotometer taken along the line XIV—XIV in FIGS. 1 and 2.

The plate 72 defines a series of elongated apertures 90 through which drive rollers extend, a pair of elongated apertures 92 through which idler rollers extend, and an optics aperture 94 aligned with the optical pick-up 75 (see FIG. 14).

The drive assembly 22 (see FIGS. 10–11) includes a drive shaft assembly 100 and a motor assembly 102. The drive shaft is secured to the motor assembly using set screws 103. The drive shaft assembly 100 includes five drive wheels 104 of uniform diameter with the wheels being evenly spaced from one another. Because the upper assembly is free to float in a vertical plane, the drive shaft assembly is also free to float in a vertical plane. The individual suspension of the idler rollers 16 under the drive rollers 104 accommodates such angular floatation.

Each of the wheels 104 defines a circumferential groove 106 (see FIG. 11). An O-ring 108, which acts as a tire, is fitted within each of the grooves 106. Each of the O-rings is fabricated of a relatively high-friction material for gripping the sample to be analyzed. The material of the preferred embodiment is precision silicone. The motor assembly 102 is generally well known in the art. The motor of the preferred embodiment is a high-torque gear motor or a stepper motor. The drive rollers 104 extend through apertures 90 to extend approximately 0.3 millimeter (mm) from the lower surface of the bottom plate 72 (see FIG. 14). As currently implemented, the drive assembly moves or pulls the sample S at a speed of approximately 3 centimeters (cm) per second.

The drive assembly 22 is secured to the bottom plate 72 by the drive bearings 110 illustrated in greatest detail in FIG. 12. Each of the drive bearings 110 is generally U-shaped, defining an interior having a circular portion 112 and a pair of opposed flat portions 114. The distance between the flat portions 114 is less than the diameter of the circular portion 112. The drive bearings 110 are fabricated of bearing-quality plastic or other resiliently deformable material. Accordingly, the legs can be spread slightly to fit the bearing over the drive shaft 100. The drive shaft then clicks into the circular portion 112. Screws 116 (FIG. 10) are inserted through holes 118 in the bearing 110 to lock the drive shaft within the circular portion 112 and to secure the bearing to the bottom plate 72. Lubricant preferably is included within the bearing 110 to facilitate rotation of the drive shaft 100.

Idler rollers 24 (see FIG. 10) are rotatably supported on the bottom plate 72 by way of bearings 120 and screws 122. The idler rollers 24 extend through apertures 92 to extend approximately 0.3 millimeter (mm) from the lower surface of the bottom plate 72 (see FIG. 14).

The media guide 130 is illustrated in FIGS. 3 and 13–14 and is a generally planar piece of relatively low-friction material. The preferred material of the present embodiment is a bearing-quality material that is soft enough to avoid damage of the sample S. As currently implemented, the material is a high-density polypropylene. As viewed in FIG. 3, the media guide is milk-can shaped having a relatively narrow forward portion 132 to fit between the idler rollers 24. The rearward portion 134 defines a central aperture 136 aligned with the optics aperture 94 in the base plate 72 and with the optical pick-up 75 of the color measurement engine 20. The media guide 130 is adhered to the bottom plate 72 using a pressure-sensitive adhesive or other suitable attachment means. The thickness of the media guide is approximately 0.3 mm so that it projects from the lower plate 72 approximately the same distance that the idler rollers 24 and the drive rollers 104 project from the lower plate 72. Consequently, the rollers 24 and 104 and the media guide 130 all lie within and define a plane.

Figure 1:
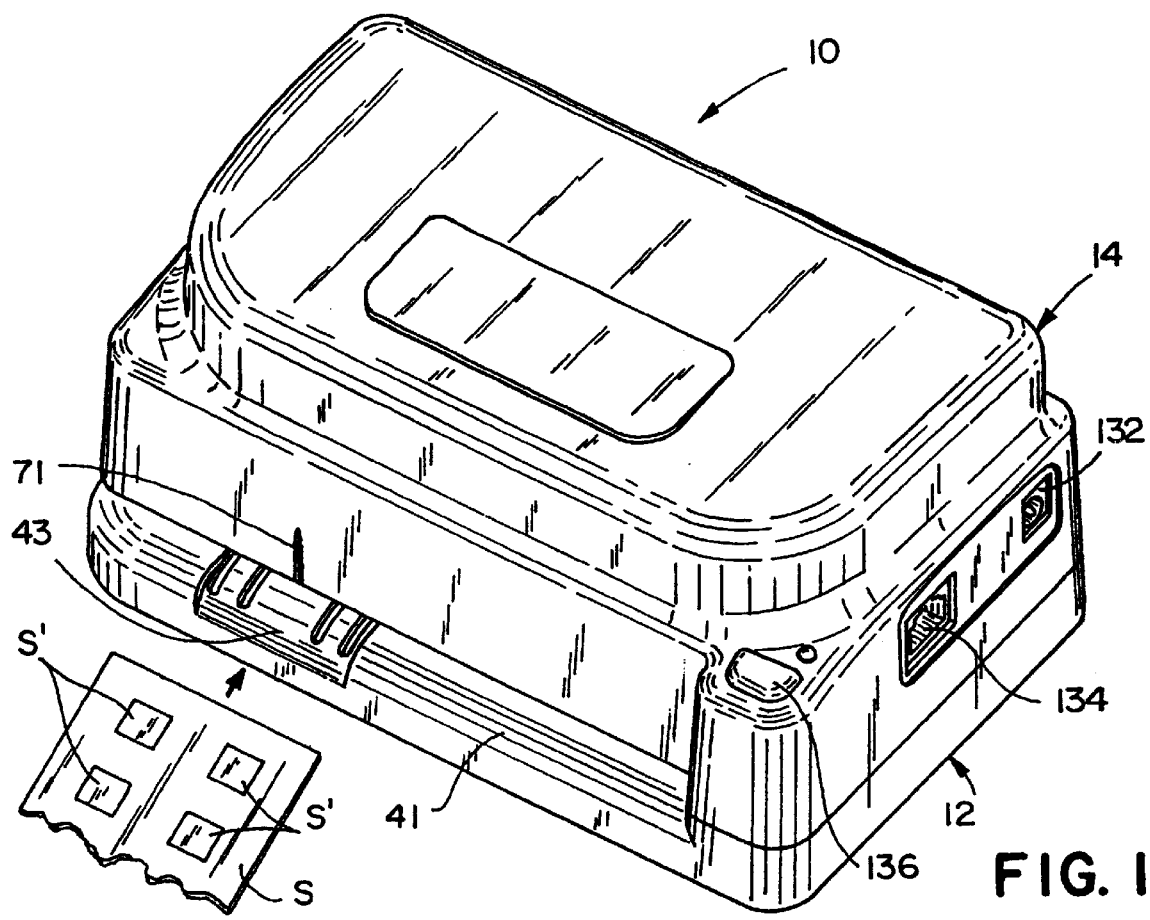
FIG. 1 is a right front perspective view of the spectrophotometer of the present invention.
Figure 2:
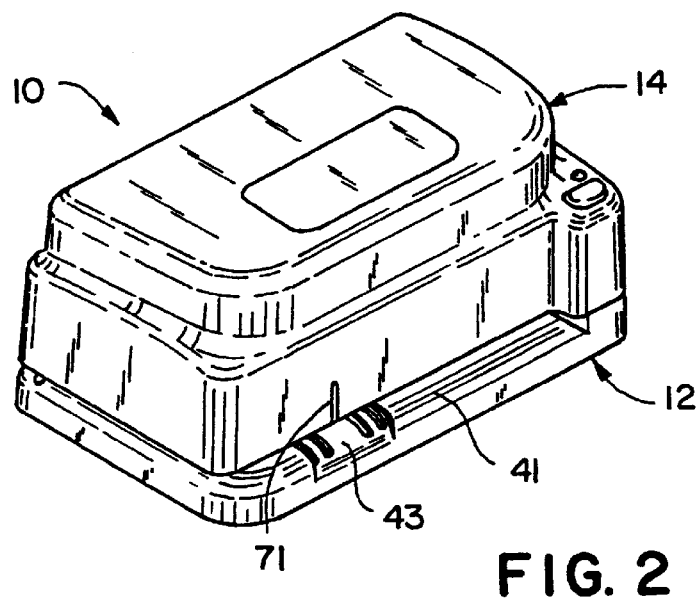
FIG. 2 is a left front perspective view of the spectrophotometer.

As seen in FIG. 1, the upper assembly further includes a 12-volt power connection 132 for powering the unit 10, an RS-232 port 134 for serial communication with a personal computer (PC) or other digital device, and a push-button 136 for actuating and operating the unit.

III. Operation

The operation of the spectrophotometer 10 is perhaps best illustrated in FIGS. 1 and 14. For purposes of reference, the area above the backer assembly 30 and below the optical pick-up 75 is referred to as the scanning station 140. The backer assembly 30 is aligned with the optical pick-up across the scanning station.

If necessary, the reflectance of the backer assembly 30 is selected by manually sliding the backer assembly to either of its two selectable positions. In the first position, the stable uniform black portion 52a of the platform 52 is presented to the color measurement engine 20. In the second position, the white light diffusing opal glass 51 in portion 52b is presented to the engine 20.

A sample S (FIG. 1), having color patches S', to be analyzed is aligned with the alignment mark 71 on the upper assembly and fed or pushed between the base 12 and the upper assembly 14. The leading edge of the sample S passes between the tension rollers 24 on the upper assembly and the idler rollers 18 on the base. The sample continues through the scanning station 140 until the forward edge of the sample S is gripped by the drive wheels 104, whereupon the sample is pulled between the drive rollers and the associated idler rollers 16. Spectral analysis or other color measurement operations are conducted on the sample S as it is drawn past the color measurement engine 20 and specifically the optical pickup 75.

As the sample moves between the idler rollers 18 and 24, the suspension arms 44 flex to permit the individual rollers 18 to move downwardly. Similarly, as the sample is drawn between the drive rollers 104 and the idler rollers 16, the individual suspension arms 40 flex to permit the rollers 16 to move downwardly. Also, the tension rollers 24 and the drive rollers 108 engage and ride along the top surface of the sample S to assist in registration of the sample with respect to the optical pick-up 75. The free floating ability of the upper assembly 14 and the individual suspension of the idler rollers 18 facilitate the accurate color measurement of samples of varying thickness. The upper assembly 14 rides along the top surface of the sample S to maintain a desired physical registration or relationship between the top surface of the sample and the engine 20.

As noted above, the tension rollers 24, the drive rollers 104, and the media guide 130 all project a substantially equal distance from the bottom plate 72. Accordingly, the media guide 130 also engages the top surface of the sample S to further assist in registration. The media guide 130 prevents flexing or bowing of the sample within the scanning station as may occur, for example, if the trailing edge of the sample is dropped below or is lifted above the level of the scanning station 140.

The spectrophotometer may be operated in either the reflective or the transmissive mode. When operated in the reflective mode, only the illuminators 77 are actuated so that the top surface of the sample S is illuminated in accordance with the ANSI standard 45°/0° reflection measurement. When operated in the transmissive mode, only the base illuminator 60 within the backer assembly 30 is actuated to illuminate the sample from beneath in accordance with the ANSI standard 180°/0° transmissive measurement.

The above descriptions are those of preferred embodiments of the invention. Various alterations and changes can be made without departing from the spirit and broader aspects of the invention as defined in the appended claims, including the Doctrine of Equivalents.

The embodiments of the invention in which an exclusive property or privilege is claimed are defined as follows:

1. A color measurement instrument comprising:
   first and second opposed assemblies defining a sample area therebetween, a first one of said first and second assemblies defining a surface facing said sample area;
   a color measurement engine supported by a second one of said first and second assemblies, said first one assembly and said second one assembly being either the same or different assemblies;
   a plurality of rollers on said first one assembly for engaging the sample to move the sample within said sample area, said rollers projecting a first distance from said surface, said first one assembly further including a media guide aligned with said color measurement engine, said media guide being planar and having a thickness approximately equal to the first distance that said rollers project from said underside, whereby said media guide also engages the sample to assist in reducing flexing and bowing of the sample.

2. A color measurement instrument as defined in claim 1 wherein said media guide comprises a relatively low-friction material.

3. A color measurement instrument as defined in claim 1 wherein said media guide defines an aperture aligned with said color measurement engine.

4. A color measurement instrument as defined in claim 1 wherein said color measurement instrument comprises a spectrophotometer.

* * * * *